United States Patent
Habouti et al.

(10) Patent No.: US 12,431,298 B2
(45) Date of Patent: Sep. 30, 2025

(54) CAPACITOR WITH CONDUCTIVE ADHESION LAYER

(71) Applicant: BIOTRONIK SE & Co. KG, Berlin (DE)

(72) Inventors: Salah Habouti, Husum (DE); Janosch Lichtenberger, Bremen (DE); Bernd Pretzlaff, Mildstedt (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/910,064

(22) PCT Filed: Mar. 15, 2021

(86) PCT No.: PCT/EP2021/056502
§ 371 (c)(1),
(2) Date: Sep. 8, 2022

(87) PCT Pub. No.: WO2021/185744
PCT Pub. Date: Sep. 22, 2021

(65) Prior Publication Data
US 2023/0094064 A1    Mar. 30, 2023

(30) Foreign Application Priority Data
Mar. 19, 2020    (EP) .................... 20164212

(51) Int. Cl.
*H01G 9/042*    (2006.01)
*H01G 9/035*    (2006.01)
*H01G 9/048*    (2006.01)
*H01G 9/08*    (2006.01)

(52) U.S. Cl.
CPC .......... *H01G 9/0425* (2013.01); *H01G 9/048* (2013.01); *H01G 9/08* (2013.01); *H01G 9/035* (2013.01)

(58) Field of Classification Search
None
See application file for complete search history.

(56) References Cited

U.S. PATENT DOCUMENTS

| 5,464,707 A | 11/1995 | Moulton et al. | |
|---|---|---|---|
| 5,728,181 A * | 3/1998 | Jung ..................... | H01M 4/02 29/623.5 |

(Continued)

FOREIGN PATENT DOCUMENTS

| GB | 894725 A1 * | 4/1962 |
| JP | 2006210883 A | 8/2006 |

OTHER PUBLICATIONS

International Search Report (PCT/ISA/210) and Written Opinion (PCT/ISA/237) mailed on Jun. 7, 2021, by the European Patent Office as the International Searching Authority for International Application No. PCT/EP2021/056502.

*Primary Examiner* — Eric W Thomas
(74) *Attorney, Agent, or Firm* — Buchanan Ingersoll & Rooney PC

(57) ABSTRACT

An embodiment of the capacitor includes a metal current collector, a conductive adhesion layer applied on the metal current collector, and an electrode active layer applied on the conductive adhesion layer, wherein the adhesion layer has a conductive non-carbide metal compound, particularly a metal oxide or metal nitride. An embodiment of the method of manufacturing the capacitor is also disclosed.

18 Claims, 5 Drawing Sheets

(56) References Cited

U.S. PATENT DOCUMENTS

| | | | |
|---|---|---|---|
| 6,201,685 B1* | 3/2001 | Jerabek | H01G 11/84 29/25.03 |
| 6,306,215 B1 | 10/2001 | Larkin | |
| 7,099,143 B1* | 8/2006 | Fife | H01G 9/0425 361/516 |
| 2001/0024700 A1* | 9/2001 | Shah | H01G 9/04 427/314 |
| 2002/0176221 A1* | 11/2002 | Hudis | H01G 9/0425 361/511 |
| 2003/0199942 A1 | 10/2003 | Nielsen et al. | |
| 2006/0286761 A1* | 12/2006 | Fife | H01G 9/035 29/25.03 |
| 2007/0211412 A1* | 9/2007 | Fife | H01G 9/0425 361/516 |
| 2008/0212260 A1* | 9/2008 | Roh | H01G 11/28 361/502 |
| 2010/0266898 A1 | 10/2010 | Yamamoto et al. | |
| 2014/0342225 A1* | 11/2014 | Isshiki | H01M 4/366 429/217 |
| 2015/0251000 A1 | 9/2015 | Kane et al. | |

\* cited by examiner

CAPACITOR WITH CONDUCTIVE ADHESION LAYER

CROSS-REFERENCE TO RELATED APPLICATIONS

This application is the United States National Phase under 35 U.S.C. § 371 of PCT International Patent Application No. PCT/EP2021/056502, filed on Mar. 15, 2021, which claims the benefit of European Patent Application No. 20164212.1, filed on Mar. 19, 2020, the disclosures of which are hereby incorporated by reference herein in their entireties.

TECHNICAL FIELD

The present invention relates to a capacitor with a stabilizing conductive adhesion layer and a method of manufacture thereof.

BACKGROUND

Particularly in aqueous electrolytic capacitors, electrode active coatings on current collectors made with binders show mechanical and electrical instabilities if directly applied on the current collector. The electrical contact resistance increases over the time, while the mechanical stability decreases. In addition, the electrolyte penetrates the porous electrode active coating and may passivate the surface of the metal.

The present disclosure is directed toward overcoming one or more of the above-mentioned problems, though not necessarily limited to embodiments that do.

SUMMARY

Based at least on the above, it is an objective of the present invention to provide a capacitor with increased mechanical and electrical stability.

At least this objective is attained by an embodiment of the capacitor having the features disclosed herein in the independent claim(s). Appropriate embodiments thereof are stated in the depended claims and in the description below.

In general, the present invention provides an electrode for a capacitor, particularly an electrolytic capacitor, or for an electrochemical cell. The electrode basically comprises:

a metal current collector,
a conductive adhesion layer applied on the metal current collector, and
an electrode active layer applied on said adhesion layer, wherein the conductive adhesion layer comprises a conductive non-carbide metal compound.

In one preferred embodiment, the electrode of the present invention acts as a cathode, for example, in a capacitor or electrochemical cell, preferably with an aqueous electrolyte. Particularly, when using the electrode of the present invention in a capacitor as cathode, anodic conditions may occur at the cathode during a discharge, which may passivate the cathode. Advantageously, the conductive adhesion layer may protect the electrode (acting as cathode) from such passivation.

Suitable embodiments of the conductive adhesion layer, the electrode active layer and the non-carbide metal compound are stated below.

An exemplary embodiment includes a capacitor, and particularly an electrolyte capacitor. The capacitor comprises:

a metal current collector,
a conductive adhesion layer applied on the metal current collector, and
an electrode active layer applied on said adhesion layer.

According to the present invention it is particularly envisioned that the conductive adhesion layer comprises a conductive non-carbide metal compound.

The term "non-carbide metal compound" particularly refers to an ionic or polar metal compound of a metal and a non-metal that does not contain carbide.

The term "electrode active layer" particularly refers to a layer or coating that is able to act as an electrode or comprise an electrode active material that is able to act as an electrode. Examples for electrode active materials include without being limited to particularly activated carbon, graphite, graphene, a carbon nanotube, and a conductive polymer.

Advantageously, the conductive adhesion layer of the present invention enables a safe and stable linkage or attachment of the electrode active layer to the metal current collector. At the same time, the conductive adhesion layer is mechanically, chemically and electrically stable, and thereby, the metal current collector is reliably protected from passivation, e.g., by the electrolyte, Moreover, the adhesion layer of the present invention can be formed at lower temperatures compared to metal carbide layers, whose manufacture require elevated temperatures, e.g., above 700° C. For example, a precursor of adhesion layer, e.g., a solution or suspensions of the non-carbide metal compound may be applied to the metal current connector and tempered below, e.g., 700° C.

Preferably, the metal current collector together with the conductive adhesion layer and the electrode active layer may act as a cathode, or as a cathodic surface in case of the capacitor is an electrolytic capacitor, in which an electrolyte forms or acts as cathode. In either case the cathodic potential is preferably on the metal collector.

According to one embodiment of the capacitor of the present invention, the non-carbide metal compound comprises a transition metal. In one embodiment, the transition metal is selected from ruthenium, niobium, iridium, manganese, zinc, titanium, zirconium, hafnium, vanadium, tantalum, molybdenum, or tungsten.

According to a further embodiment, the capacitor of the present invention further comprises an anode essentially consisting of or comprising a valve metal, particularly selected from tantalum, niobium or aluminium.

According to a further embodiment, the capacitor further comprises an aqueous electrolyte. In one embodiment, the electrolyte comprises ethylene glycol and optionally an acid, particularly boric acid or acetic acid, particularly in case of the anode is formed by aluminium or tantalum. In one embodiment, the electrolyte comprises ethylene glycol, acetic acid and ammonium acetate. In one embodiment, the electrolyte comprises dimethylformamide, dimethylacetamide and/or gamma-butyrolactone. In one embodiment, the electrolyte comprises tetracyanoquinodimethane, polypyrrole, or poly(3,4-ethylenedioxythiophene).

According to a further embodiment of the capacitor of the present invention, the non-carbide metal compound is a metal oxide. In one embodiment, the adhesion layer comprises ruthenium oxide, niobium oxide, iridium oxide, manganese oxide, zinc oxide and mixtures thereof.

According to a further embodiment of the capacitor of the present invention, the non-carbide metal compound is a metal nitride. In one embodiment, the adhesion layer comprises titanium nitride, zirconium nitride, hafnium nitride, vanadium nitride, niobium nitride, tantalum nitride, molybdenum nitride, tungsten nitride, or a mixture thereof.

Preferably, the adhesion layer is structured, particularly in the nanometre range, i.e., the adhesion layer comprises spherical or rod-shaped particles with a size in the range of, e.g., 10 nm to 100 nm.

In one embodiment, the metal oxide is a metal dioxide ($MO_2$), particularly of a transition metal. Preferred metal oxides are able to form a nanostructure, for example, titanium oxide ($TiO_2$), ruthenium oxide ($RuO_2$), iridium oxide ($IrO_2$), niobium oxide ($NbO_2$), or manganese oxide ($MnO_2$).

According to a further embodiment of the capacitor of the present invention, the adhesion layer is characterized by a thickness in the range of 10 nm to 5 µm. In one embodiment, the adhesion layer is characterized by a thickness in the range of 40 nm to 0.4 µm.

According to a further embodiment of the capacitor of the present invention, the electrode active layer comprises a conductive material selected from carbon, particularly activated carbon, graphite, graphene, a carbon nanotube, and/or a conductive polymer.

According to a further embodiment of the capacitor of the present invention, the conductive layer comprises a binder. In one embodiment, the binder is selected from polyvinylidene fluoride (PVDF) polytetrafluoroethylene (PTFE), carbomethyl cellulose (CMC) or a rubber, particularly acryl rubber, nitrile butadiene rubber, styrene butadiene rubber (SBR) or butyl rubber.

According to a further embodiment of the capacitor of the present invention, the metal collector comprises or essentially consists of titanium or a titanium alloy.

According to a further embodiment, the electrolytic capacitor comprises a metal housing, wherein at least a part of the metal housing forms the metal collector. Advantageously, the cathodic potential is on the metal housing, thereby the cathode is contactable from the outside of the capacitor via the housing. Preferably, the metal housing and thus the metal collector essentially consists of or comprises titanium or a titanium alloy.

According to a further embodiment, the capacitor of the present invention further comprises at least one separator element. Such separator element is particularly configured to provide mechanical separation of the electrodes. In one embodiment, the at least one separator element is arranged between the anode and the current collector. In one embodiment, the at least one separator element is designed as being at least semipermeable for charge carriers, e.g., charge carrier of an electrolyte. In one embodiment, the at least one separator element is formed of expanded or porous polytetrafluoroethylene, polypropylene, polyethylene, or a mixture of polypropylene and polyethylene.

An exemplary embodiment includes a method for manufacturing a capacitor, and particularly for manufacturing the capacitor of the present invention. The method comprises the steps of:

applying a conductive adhesion layer on a metal current collector, and applying an electrode active layer on the conductive adhesion layer.

According to the present invention it is particularly envisioned that the conductive adhesion layer comprises a conductive non-carbide metal compound, particularly a metal oxide or metal nitride.

Suitable non-carbide metal compounds are stated in the above embodiments of the capacitor of the present invention.

According to one embodiment of the manufacturing method of the present invention, the conductive adhesion layer is applied on the metal current collector in form of a solution or a suspension, wherein the solution or the suspension comprises the non-carbide metal compound and an organic solvent, wherein after application of the adhesion layer the metal current collector together with the adhesion layer is tempered. In one embodiment, the metal current collector together with the adhesion layer is tempered at a temperature below 700° C., particularly at a temperature in the range of 360° C. to 550° C.

Advantageously, the conductive adhesion layer may be formed by a lower temperature when compared to the temperature required for the formation of a carbide layer. At the same time, a stable and porous or nanostructured conductive adhesion layer can be obtained, which protects the metal current collector from passivation and facilitates a reliable attachment of the subsequently applied electrode active layer.

According to further embodiment of the manufacturing method of the present invention, the electrode active layer is applied in form of a composition comprising a conductive material, particularly carbon, particularly activated carbon, graphite. graphene, carbon nanotubes, and/or a conductive polymer, and optionally a binder, wherein after applying the electrode active layer, the metal current collector together with the conductive adhesion layer and the electrode active layer is tempered. In one embodiment, the metal current collector together with the conductive adhesion layer and the electrode active layer is tempered at a temperature below 700° C. after application of the electrode active layer, particularly at a temperature in the range of 80° C. to 240° C.

Suitable conductive materials and binders are stated in the above embodiments of the electrolytic capacitor of the present invention.

Preferably, the composition comprising the conductive material is applied in form of a paste, which is more easily applicable to the surface of the metal current collector or the adhesion layer, respectively.

An exemplary embodiment includes a medical device, and particularly an implantable medical device. The medical device comprises the capacitor of the present invention or a capacitor obtainable by the manufacturing method of the present invention. In one embodiment, the medical device is a pacemaker, a cardioverter/defibrillator, a loop recorder or a sensor.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further advantages, features and embodiments of the present invention will be explained hereinafter with reference to the drawings, in which.

DETAILED DESCRIPTION

Examples

In a preferred embodiment of the present invention, a conductive metal oxide is applied between a current collector (housing) of a cathode (e.g., of a capacitor) and an additional electrode active coating or layer. This interlayer increases the adhesion of the electrode active coating or layer to the metal current collector and protects the metal current collector from passivation. Particularly, the conductive metal oxide applied as interlayer acts as an adhesion promotor for the electrode active layer, particularly due to its nano-structured surface, and prevents a passivation of the current collector because of its mechanical and chemical stability.

Accordingly, the present invention provides a mechanically, electrically and chemically stable active layer or coating for a cathode with a high capacitance, which protects a substrate acting as current collector (e.g., titanium housing) from passivation and enables a reliable, long-term stable attachment of an electrode active layer or coating to the substrate.

Advantageously, such active layer or coating can be manufactured without elevated temperatures (e.g., above 700° C.), which are disadvantageous in terms of costs and impairments of components (warpage of the substrate, housing, cover, etc.; grain growth; large grains can impair the mechanical stability and tightness of components to welded, e.g., housing and cover).

Figure 1:
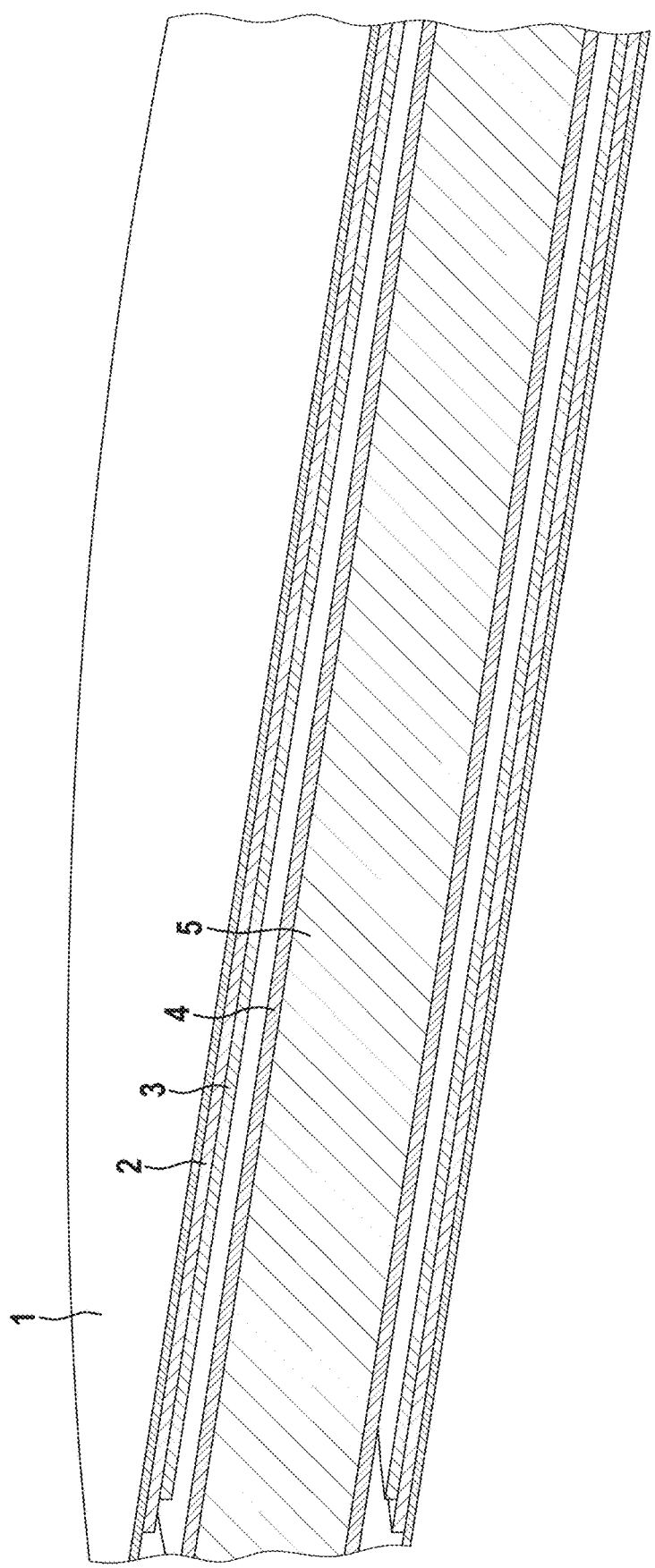
FIG. 1 shows a schematic drawing of the current collector of the capacitor of the present invention.

FIG. 1 illustrates the basic structure of an embodiment of capacitor of the present invention. The capacitor comprises a titanium housing 1, which acts as a current collector. On an inner surface of the housing 1, a metal oxide layer 2 is applied, e.g., ruthenium or iridium oxide, on with a further electrode active layer 3, e.g., activated carbon with a suitable binder, is coated. The capacitor further comprises an anode essentially consisting of or comprising an oxide forming metal 5. Such metal may be a valve metal such as tantalum, aluminium or niobium. The capacitor further comprises a separator 4 to avoid direct electrical contact of the anode 5 with the electrode active layer. Furthermore, an electrolyte fills the space between the anode and the coated titanium housing and establishes thereby an electric contact. Particularly, the afore-mentioned separator is soaked with the electrolyte.

For manufacturing thereof, a titanium housing 1 was coated with a conductive metal oxide 2, e.g., ruthenium or iridium oxide, and subsequently an electrode active layer 3 comprising activated carbon with a suitable binder (PVDF) was applied. The thereby manufactured graphite electrode is mechanically and electrically long-term stable in an aqueous electrolyte. The long-term stability was investigated and confirmed at elevated temperatures.

The manufacturing of the ruthenium oxide layers were conducted with a coating liquid consisting of a metal salt solved or dispersed in an organic solvent. After coating, the precursor substance was converted at temperatures between 360° C. and 500° C. The obtained RuOx-layers had a thickness in the range of 0.04 µm to 0.4 µm, and were fully crystalized, electrically conductive and mechanically very stable. In a second step, a paste containing activated carbon and a suitable binder was applied on the metal oxide coated titanium surface and tempered.

In this example, the ruthenium oxide layers were manufactured with a solution of 10 mmol/l to 200 mmol/l ruthenium (III) chloride hydrate in methanol. After coating the precursor was converted and annealed in a furnace at temperatures between 360° C. and 500° C. The obtained RuOx layers had a thickness in the range of 0.04 µm to 0.4 µm, were fully crystalized, electrically conductive and mechanically very stable. In a second step, a coating of activated carbon and PVDF in an organic solvent was applied on the metal oxide coated titanium surface and annealed at a temperature of 200° C.

Figure 2:
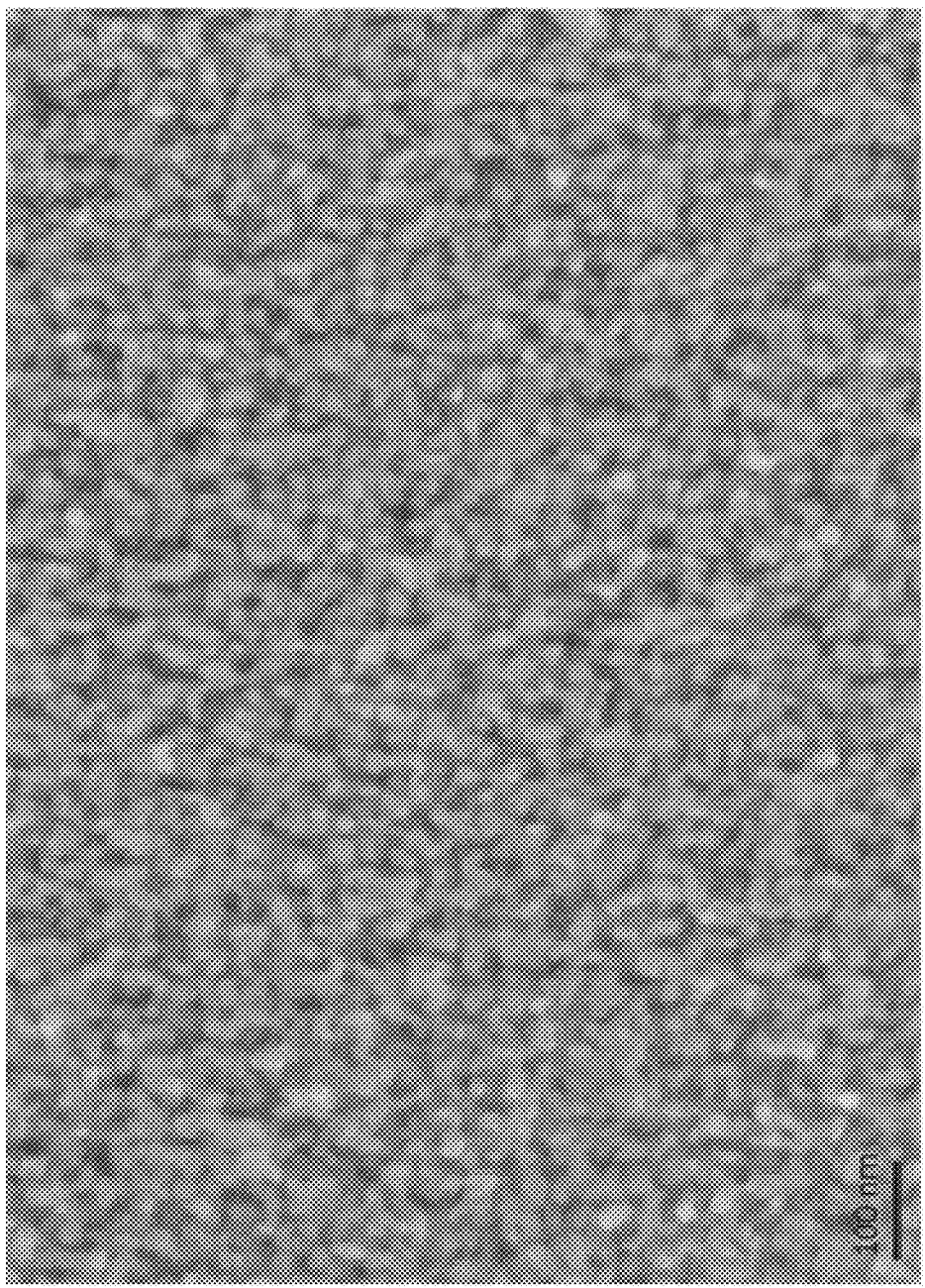
FIGS. 2 and 3 show scanning electron microscopic images of nano-structured ruthenium oxide coated surfaces.
Figure 3:
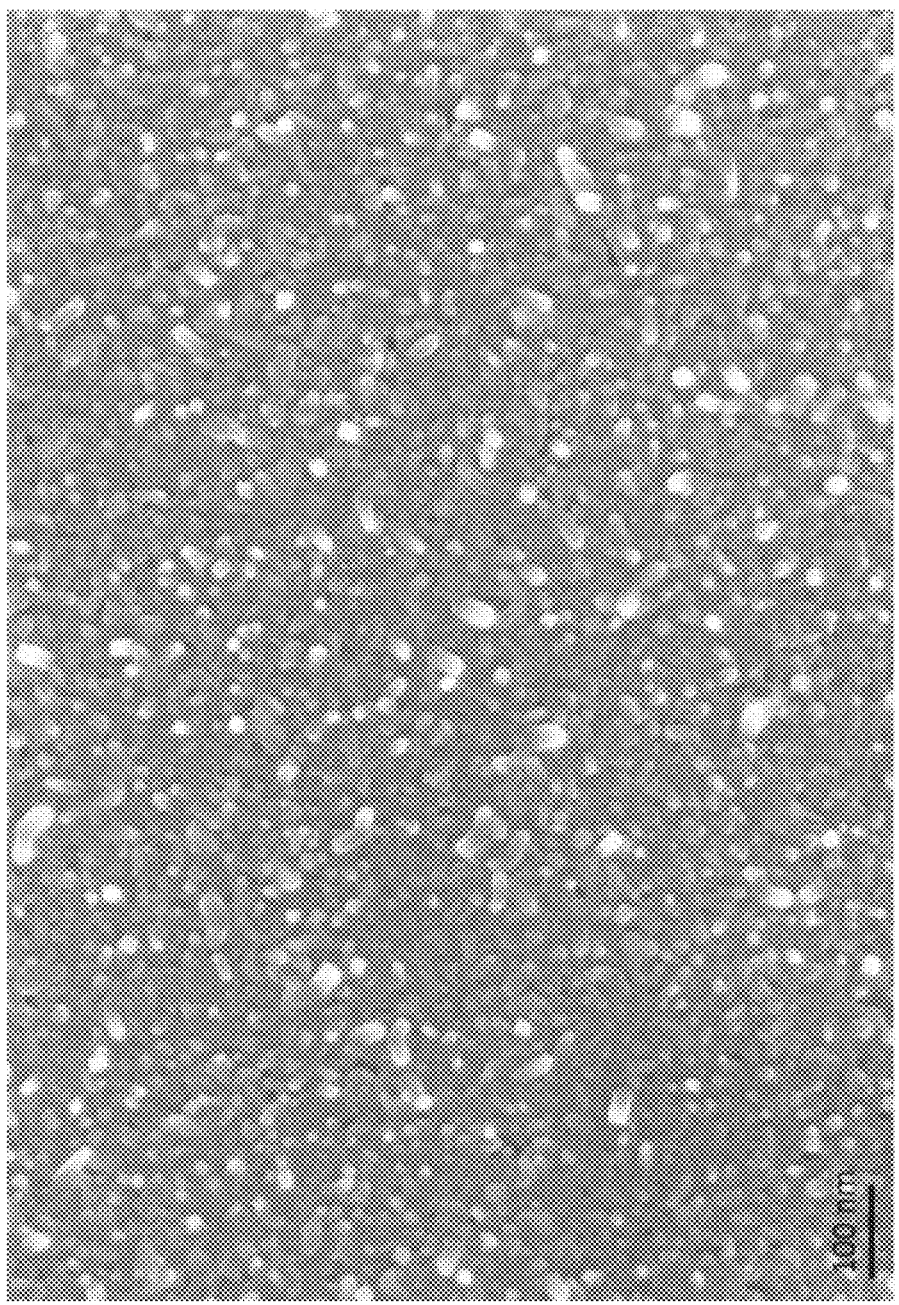
Figure 4:
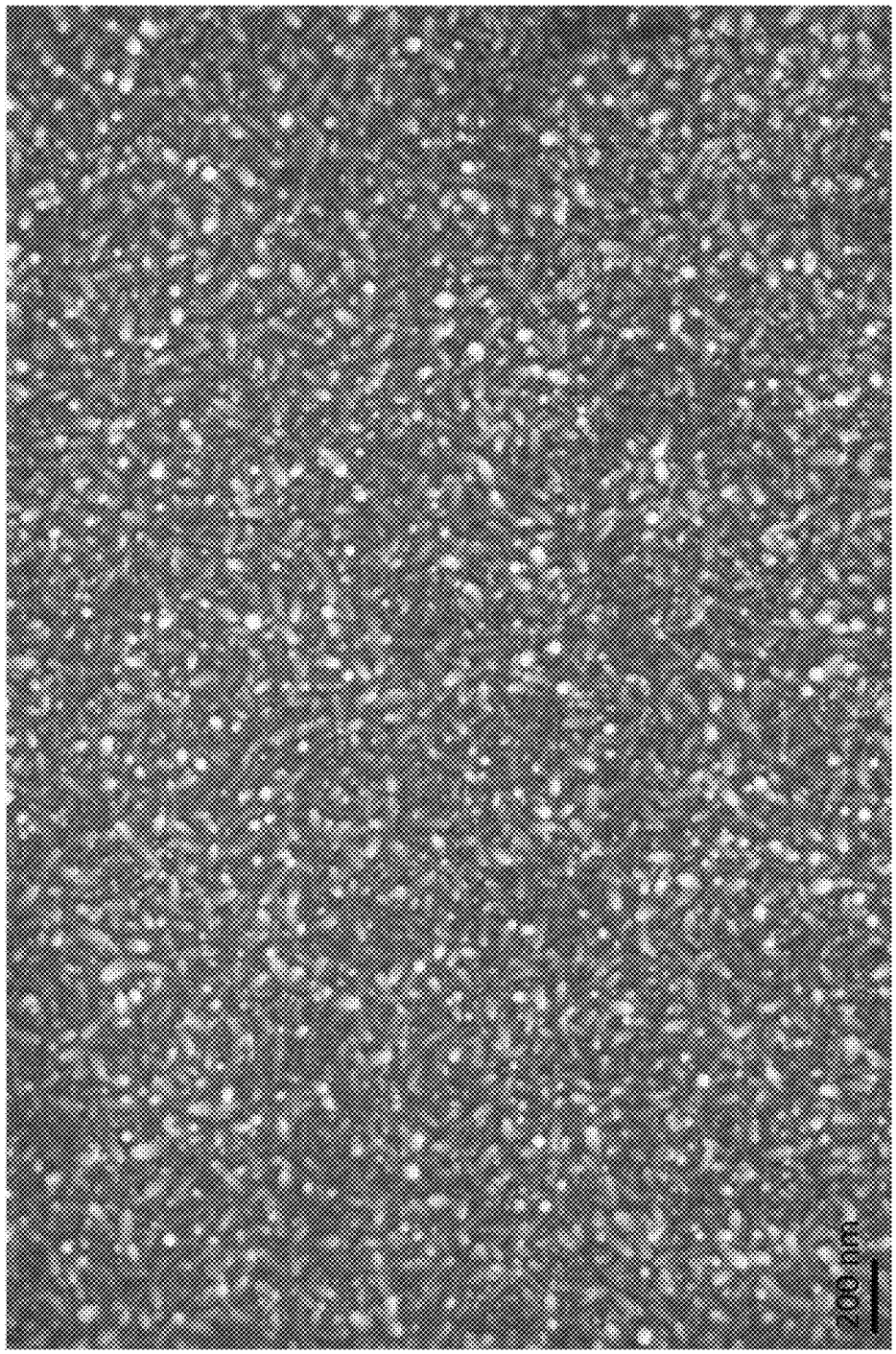
FIG. 4 shows a scanning electron microscopic image of a nano-structured iridium oxide coated surface.

FIGS. 2 and 3 show scanning electron microscopic images of nano-structured ruthenium oxide coated surfaces. In FIG. 2, the surface exhibits spherical and cylindrical structures or particles with an approx. size of 10 nm. As can be seen in FIG. 3, a different process control, in which a thicker ruthenium oxide layer was applied, resulted in a formation of nanowires that are larger than 50 nm. This structure is likewise porous. FIG. 4 shows a scanning electron microscopic image of a nano-structured iridium oxide coated surface.

Figure 5:
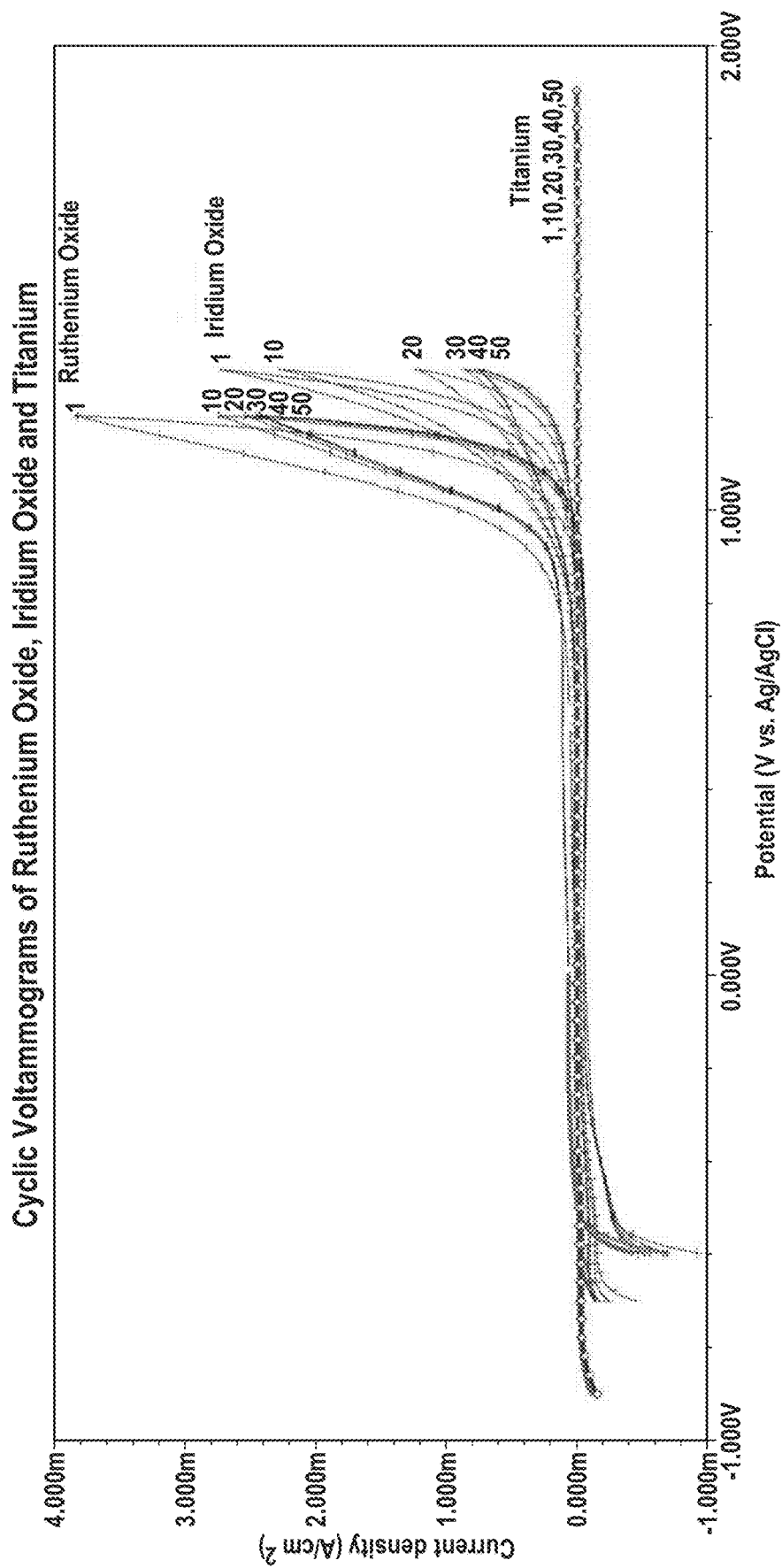
FIG. 5 shows cyclic voltammograms of titanium substrates with nano-porous ruthenium oxide, nano-porous iridium oxide coatings and without a coating.

FIG. 5 shows cyclic voltammograms of titanium substrates that have been coated with ruthenium oxide or iridium oxide as well as an uncoated substrate. While the uncoated titanium substrate becomes passivated upon anodic polarisation and even at higher depolarisation no current flows, both ruthenium and iridium oxide coated substrates remain active, while the current density remains stable without any passivation. The voltammograms have been obtained using a test electrolyte containing 120:80:30 (volume fractions) of ethylene glycol, water and acetic acid with 12 weight fractions of ammonium acetate and 10 mmol/l KCl. Voltages were determined in relation to an Ag/AgCl reference electrode.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. A wet electrolyte capacitor, comprising:
    a cathode, the cathode comprising:
        a cathode metal current collector,
        a nanostructured conductive adhesion layer applied on said cathode metal current collector, and
        an electrode active layer applied on said nanostructured conductive adhesion layer,
        wherein said nanostructured conductive adhesion layer comprises a conductive non-carbide metal compound, said conductive non-carbide metal compound comprises a metal nitride or a metal oxide,
        wherein said electrode active layer includes a binder.

2. The capacitor according to claim 1, wherein:
    said non-carbide metal compound includes a transition metal, said transition metal selected from ruthenium or iridium.

3. The capacitor according to claim 1, further comprising:
    an anode, wherein said anode:
        comprises a valve metal, said valve metal including tantalum, or niobium.

4. The capacitor according to claim 1, further comprising an aqueous electrolyte.

5. The capacitor according to claim 1, wherein said nanostructured conductive adhesion layer comprises:
- a metal oxide, said metal oxide including ruthenium oxide, iridium oxide, or a mixture thereof; and/or
- said metal nitride includes titanium nitride, zirconium nitride, hafnium nitride, vanadium nitride, niobium nitride, tantalum nitride, molybdenum nitride, tungsten nitride, or a mixture thereof.

6. The capacitor according to claim 1, wherein said nanostructured conductive adhesion layer has a thickness in the range of 1 nm to 5 μm.

7. The capacitor according to claim 1, wherein said electrode active layer comprises a conductive material selected from carbon, said carbon selected from activated carbon, graphite, graphene, and/or carbon nanotubes.

8. The capacitor according to claim 1, wherein the binder is selected from polyvinylidene fluoride (PVDF) polytetrafluoroethylene (PTFE), carbomethyl cellulose (CMC) or a rubber.

9. The capacitor according to claim 1, wherein said metal current collector:
- comprises titanium or a titanium alloy.

10. The capacitor according to claim 1, further comprising a metal housing, wherein at least a part of said metal housing forms said metal current collector.

11. Method for manufacturing said capacitor according to claim 1, comprising the steps of:
- applying said nanostructured conductive adhesion layer on said metal current collector, and
- applying said electrode active layer on said nanostructured conductive adhesion layer, wherein said nanostructured conductive adhesion layer comprises said non-carbide conductive metal compound,
- wherein said nanostructured conductive adhesion layer is applied on said metal current collector in form of a solution or suspension, wherein said solution or said suspension comprises said non-carbide metal compound and an organic solvent, wherein after application of said nanostructured conductive adhesion layer said metal current collector is tempered at a temperature below 700° C.

12. The method according to claim 11, wherein said electrode active layer is applied in form of a composition, including a paste, comprising a conductive material, including carbon and activated carbon, graphite, graphene, and/or carbon nanotubes, wherein after applying said electrode layer said metal current collector is tempered at a temperature below 400° C.

13. An implantable medical device, comprising said capacitor manufactured by said method according to claim 11.

14. The method according to claim 11, wherein said metal current collector is tempered at a temperature in the range of 360° C. to 550° C.

15. The method according to claim 11, wherein said electrode active layer is applied in form of a composition, including a paste, comprising a conductive material, including carbon and activated carbon, graphite, graphene, and/or carbon nanotubes, wherein after applying said electrode layer said metal current collector is tempered at a temperature in the range of 80° C. to 240° C.

16. An implantable medical device, comprising said capacitor according to claim 1.

17. The capacitor according claim 1, wherein said nanostructured conductive adhesion layer has a thickness in the range of 40 nm to 0.4 μm.

18. The capacitor according to claim 1, wherein the nanostructured adhesion layer comprises spherical or rod-shaped particles with a size in the range of 10 nm to 100 nm.

* * * * *